(12) United States Patent
Geloen

(10) Patent No.: US 10,130,523 B2
(45) Date of Patent: Nov. 20, 2018

(54) SELF-CONTAINED ELECTRONIC DEVICE FOR DETECTING AND ALERTING OF THE SATURATION OF A PROTECTION LAYER ARTICLE FOR UROFECAL INCONTINENCE

(71) Applicant: Jacques Geloen, Bondues (FR)

(72) Inventor: Jacques Geloen, Bondues (FR)

(*) Notice: Subject to any disclaimer, the term of this patent is extended or adjusted under 35 U.S.C. 154(b) by 330 days.

(21) Appl. No.: 14/778,847

(22) PCT Filed: Mar. 25, 2014

(86) PCT No.: PCT/FR2014/050698
§ 371 (c)(1),
(2) Date: Sep. 21, 2015

(87) PCT Pub. No.: WO2014/154998
PCT Pub. Date: Oct. 2, 2014

(65) Prior Publication Data
US 2016/0045378 A1 Feb. 18, 2016

(30) Foreign Application Priority Data
Mar. 27, 2013 (FR) ..................................... 13 00711

(51) Int. Cl.
*G08B 23/00* (2006.01)
*A61F 13/42* (2006.01)
(Continued)

(52) U.S. Cl.
CPC .............. *A61F 13/42* (2013.01); *A61B 5/202* (2013.01); *A61F 5/48* (2013.01); *H01M 6/34* (2013.01);
(Continued)

(58) Field of Classification Search
CPC ...... A61F 13/42; A61F 2013/424; A61F 5/48; A61B 5/202; A61B 5/6804; H01M 6/34
(Continued)

(56) References Cited

U.S. PATENT DOCUMENTS

| | | | | |
|---|---|---|---|---|
| 4,768,023 A | * | 8/1988 | Xie | A61F 13/42 340/573.5 |
| 5,036,859 A | * | 8/1991 | Brown | A61F 5/48 128/886 |

(Continued)

FOREIGN PATENT DOCUMENTS

| | | |
|---|---|---|
| EP | 270 048 A1 | 6/1988 |
| WO | 2007/070267 A1 | 6/2007 |

(Continued)

*Primary Examiner* — John A Tweel, Jr.
(74) *Attorney, Agent, or Firm* — Dilworth & Barrese, LLP

(57) ABSTRACT

The invention relates to a self-contained electronic device for detecting and alerting of the saturation of a protection layer article used for urofecal incontinence, including at least one self-contained electrical generator module comprising an arrangement of pairs of elements having metal electrodes that are electrically connected to one another and distributed over a predetermined inner area of the article, made of zinc-copper in particular, intended for generating a current upon contact with an acidic and aqueous urofecal medium by means of a redox reaction, in order to electrically control, in a self-contained manner, the inner and outer means for giving notification of the saturation, in particular light means, sound means, or means for analogue or digital transmission of wired or wireless signals. The invention is useful in a protection layer article for urofecal incontinence for seniors or infants.

22 Claims, 4 Drawing Sheets

(51) Int. Cl.
 *A61F 5/48* (2006.01)
 *A61B 5/20* (2006.01)
 *H01M 6/34* (2006.01)

(52) U.S. Cl.
 CPC ... *A61F 2013/424* (2013.01); *H01M 2220/30* (2013.01)

(58) Field of Classification Search
 USPC .................................................. 340/573.5
 See application file for complete search history.

(56) References Cited

U.S. PATENT DOCUMENTS

| | | | |
|---|---|---|---|
| 7,250,547 B1* | 7/2007 | Hofmeister | A61F 13/42 340/573.5 |
| 9,283,123 B2* | 3/2016 | Lewis | A61F 13/42 |
| 2007/0142797 A1* | 6/2007 | Long | A61F 13/42 604/361 |
| 2010/0122391 A1 | 5/2010 | Chao | |
| 2010/0305530 A1* | 12/2010 | Larkin | A61F 13/42 604/361 |
| 2012/0040655 A1* | 2/2012 | Larkin | A61F 13/42 455/418 |
| 2014/0200538 A1* | 7/2014 | Euliano | A61F 13/42 604/361 |

FOREIGN PATENT DOCUMENTS

| WO | 2011/054045 A1 | 5/2011 |
|---|---|---|
| WO | 2011/126497 A1 | 10/2011 |
| WO | 2013/013197 A1 | 1/2013 |

\* cited by examiner

SELF-CONTAINED ELECTRONIC DEVICE FOR DETECTING AND ALERTING OF THE SATURATION OF A PROTECTION LAYER ARTICLE FOR UROFECAL INCONTINENCE

SUMMARY OF THE INVENTION

The present invention makes it possible to see at a distance whether a protection used for adult and pediatric urofecal incontinence is saturated.

The invention consists in integrating a generator module into the absorbent thickness of a protection, said generator module being associated with an external indicator module. The last element forming the current generator is located at the dorsal boundary of the absorbent zone in order to turn on the device like a switch when the protection is completely saturated. This module generates a current under the influence of acid urine making contact with paired copper/zinc electrodes. This gradually increasing current, which however is delivered all-or-not, is capable of ensuring either a light-emitting diode at the bedside of the patient is turned on or any electronic or I.T. remote management interface is activated.

The aim is to objectify with certainty the need for a change in order to prevent cutaneous problems with elderly or young fragile patients. The underlying problem i.e. the need for sleep to be respected in institutions under the "humanitude" principle (a care-giving method developed in France that emphasizes respect for the patient) is solved, the carer being capable of seeing the indicator at the bedside of the patient without turning on the lights of the room and without uncovering the patient to observe colorimetric marks located inter-thigh and on his back. An indicator that is on will lead to a saturated protection being changed. An indicator that is off, during the nightshift, will allow the carer to respect the sleep of the patient.

The frequency of incontinence in institutions is estimated at 70% of residents. The exponential increase in the number of senior citizens hints at the potential industrial impact. The addition of these generator/indicator modules to protections will greatly improve the comfort of the elderly and the not so elderly.

At the present time, saturation indicators use a chemical colorimetric method taking the form of marks extending from the inter-thigh of the patient to his lumbar region. The indicators change from blue to yellow on contact with urine. Obviously, visual inspection of these indicators requires the patient to be moved, their covers to be removed and, at night, there to be enough illumination, thereby necessarily meaning the patient has to be woken up. One can imagine the consequences of these nocturnal checks on demented residents or residents suffering from psychiatric problems who, once woken up, have no desire to go back to sleep.

Moreover, the "humanitude" principle requires the sleep of residents living in institutions be respected, thereby making it impossible to check colorimetric indicators during nocturnal and diurnal sleep phases. In addition, the underlying problem creates a dilemma that is shared by teams of carers:

some carers completely respecting the "humanitude" principle and do not wake patients and therefore do not check for saturation at the risk of severe cutaneous complications (redness, superinfections, mycosis, pressure ulcers) as a result of maceration of the skin of patients left soaking in their own urine; and some carers systematically wake residents to check indicators in order to prevent cutaneous problems, such checks sometimes being unnecessary as the protection is still dry. In this case the "humanitude" principle is not respected.

It would also seem important to note the rivalries induced by these different practices, carers of the second group accusing those of the first of not changing patients and of lazily leaving work for the following shift, and those of the first group objecting to waking patients who then will not go back to sleep.

One aim of the invention is to make it possible to see whether a protection is saturated, without waking the patient, by way of a visual, sonic, mechanical or electromagnetic indicator located at a distance from the patient. Thus, the patients in question will be changed in good conscience when the indicator is activated, this indicating a completely saturated protection.

The current generator is composed of an arrangement of metal zinc/copper pairs connected in series and separated from each other by a space ensuring the autonomy of the pairs by preventing any electrical interference between them. The novel arrangement of the current generator included in the thickness of the absorbent liner of the protection is chosen in order to generate a voltage that gradually increases but that is delivered, to activate the indicator, only when the liner has completely saturated (on/off configuration). The carer will then wake the resident to make the required change, thus avoiding any potential cutaneous problems. The "humanitude" principle is furthermore respected as only patients whose protection is saturated will be changed, all those whose indicator remains inactive being able to continue their night normally as their protection is not completely saturated.

The principle of this external indicator means there is no need to check indicators located on the backs of patients, the current generator ensuring this function being placed, in part, facing this zone. By choosing a luminous visual indicator the sleep of patients will be respected, in particular at night during the rounds of care assistants. In this context, the rules of "humanitude" are respected.

Moreover, one can imagine already the potential savings realizable if changes are only made on complete saturation, which is not presently the case, as overnight inspections and awakenings often lead to protections that are only a quarter or half saturated being changed.

The invention relates to an autonomous electronic device for detecting and signaling the saturation of a protective liner type article intended for urofecal incontinence, comprising at least one autonomous electrical generator module comprising an arrangement of pairs of especially zinc/copper metal electrode elements that are electrically connected to one another and distributed over a preset internal zone of the article, intended to generate a current on contact with an aqueous and acid urofecal medium via a redox reaction in order to electrically and autonomously control internal or external means for signaling the saturation, these means especially being luminous or sonic means or wired or wireless digital or analog means for transmitting signals, etc.

According to particular embodiments:

the pairs of formatted metal electrode elements are connected in series electrically with a minimum distance between each pair preventing interactions, the output connection terminals being the first electrode of the first pair and the second electrode of the last pair.

each electrode element made up of parallel strips of a pair being separated one from the other by a parallel space receiving the urofecal medium, ensuring the autonomy of the pairs by preventing any electrical interference between them.

the last pair of electrodes of the arrangement is located in the dorsal boundary portion of the protection in order to provide the generator assembly with an "on/off switch" function that is activated when the latter element is wetted in order to indicate the saturation of the protective liner type article.

the assembly is completely or partially integrated into a textile envelope comprising pores in zones especially facing spaces separating the electrodes.

the electrical generator module comprises a thin flexible printed circuit board type structure comprising one or more sides of conductive tracks of one or more materials.

the signaling means comprise at least one internal or external light-emitting diode powered only by the generator module.

the signaling means comprise at least one internal light source of the light-emitting diode type associated optically with an optical fiber type means for transmitting the information over distance.

the electrical generator module extends along the longitudinal central axis of the protective liner type article intended for incontinence with at least one major portion located toward the back portion of the article.

the electrical generator module has a strip format (especially of 30 cm) consisting of an arrangement of electrode pairs perpendicular and symmetric relative to the central axis (especially of 2 cm on either side), the pairs being spaced apart by a preset distance (especially of 4 cm).

The invention is composed of two portions:

a current generator integrated into the absorbent thickness of the protection having the technical particularity of inducing a voltage that increases in steps as the imbibition progresses. However, this generated voltage will be exploited at the terminals of the system only on complete impregnation of the protection indicating complete saturation; and an external indicator, a visual indicator in this version, placed at a distance from the patient and connected to the generator module by a thin insulated bipolar conductive wire. Variants are envisioned further on in the description.

The system consists in generating a current created by an arrangement of regularly spaced, series-connected metal pairs, or units, that form zinc/copper batteries when submerged in an acid aqueous medium. In acid media the metals of the electrodes of the generator sustain redox reactions as said metals are of different natures. It is possible to imagine a multitude of metal pairs possibly being the origin of such redox reactions in an acid medium. However, empirically, zinc/copper pairs give the best results in terms of electromotive force. This generator, placed and included in the absorbent liner of the protection, is used to turn on a light-emitting diode LED or other indicator. Urine is an ideal acid solution with a pH oscillating between 4 and 6. The units, each of which consists of one flat wire made of copper and one flat wire made of zinc, which wires are parallel and separated by a thin void, are fastened to a textile (inter alia) carrier that holds the electrodes and maintains the required resistive space between the pair. A sheathed conductor is then used to form an insulated connection between the units, in order to obtain a generator producing the current in the vicinity of 2 volts and a few milliamps required for the LED.

The last unit, placed in the dorsal boundary portion of the absorbent liner, which unit is the last impregnated by the urine, plays the role of a contactor inducing the activation of the indicator. With this arrangement, the indicator will be activated if and only if the last element is wetted and therefore conductive, thereby preventing protections that are only half saturated from being changed. The current produced gradually increases as the elements of the generator are in turn impregnated, then is finally delivered when the last element (forming the autonomous on/off switch of the system) is wetted.

For reasons of cost, the case of a luminous indicator will be dealt with in this description but other interfaces may be employed: sonic, I.T., mechanical, electromagnetic, etc.

In the example, the wired indicator formed by the light-emitting diode, its bipolar conductive wire and the miniature connector connecting it to the generator will be installed at the bedside of the patient. The LED diode will be placed at a distance from the patient in order to be visible by the carer during his nightly round. The miniature connector used is placed on the front side of the protection in order to prevent any pressure-induced cutaneous injury while asleep.

The indicator device will be reusable in its sterilizable version in order to decrease costs as much as possible. The components: wires, interconnections and contactors, are flexible and innocuous in order to prevent any injury or mishandling.

The light-emitting diode (LED) located remotely from the generator may also be incorporated into the protection facing the connector. In this case, the photons emitted by the diode will be transferred by an optical fiber fastened to the diode, the end of which will be placed a distance away from the patient. The light source is then integrated into the protection and the light is conveyed over a distance by the optical fiber to the bedside of the patient. This method, which is very economical, simplifies the connection procedure.

Depending on the manufacturing method, variants may be envisioned:

other metals may be used to produce the elements of the current generator. However, the copper/zinc pair seems the most appropriate with an efficiency and an electromotive force higher than aluminum/copper or lead/copper pairs in acid media. Chemical units may also be envisioned to produce the required power. The arrangement induces a voltage that increases in steps as a function of the gradual imbibition of the pairs.

the number of cells may vary depending on the desired voltage and current. Likewise, the area of the metal electrodes making contact with the acid medium and the inter-electrode distance affect the final current delivered. Regarding the generator, the use of a thin flexible epoxy sheet (printed circuit board type) integrating the copper electrode (copper track) and the zinc electrode (adhesively bonded to the epoxy carrier) separated by the smallest possible space, would seem to be one way of facilitating industrial production during the assembly of the elements of the generator. The zinc/copper pairs will be connected together by a track insulated by a lacquer. The imbibition of the electrodes of the pair will be achieved by direct contact with the absorbent material of the protection overlaid on the epoxy sheet. This flexible generator, which is therefore compatible with the movements of the body, induces a voltage that increases in steps as a function of the gradual imbibition of the pairs. The on/off function of the last element located facing the dorsal region is retained, ensuring the activation of the luminous, electromagnetic, I.T. or mechanical inter alga external indicator.

the biased light-emitting diode may be replaced by any other electronic device, such as a J-K CMOS flip-flop triggering circuit or an operational amplifier, capable of controlling a mechanical (relay), electromagnetic or I.T. interface of any type. The current delivered may also serve to control a telephonic microwave emitter module integrated into the protection. The final cost will of course be the main parameter limiting possible extensions.

the urine and/or water of the stool are the fundamental elements required to activate a generator consisting of an arrangement of copper/zinc pairs. The pH must be acid. However, with a view to instances of neutral or alkaline urinary pH, a weak oxalic, tartaric or citric acid added in powder form to and making contact with the electrodes of the pairs will compensate for this deficiency during its aqueous dissolution. Production is simply by dip coating of the electrodes in the weak acid powder during the phase of mounting on the textile carrier or flexible epoxy.

the metal electrodes forming the generator will be held either using an, optionally adhesive, semipermeable flexible textile film or on a flexible epoxy printed circuit board. Pores will be produced facing the spaces separating the metal electrodes in the textile version, such pores not being necessary in the printed circuit board version. These orifices (perforated during manufacture) allow the urine to pass in order to better imbibe the copper/zinc pairs.

the semipermeable textile prevents interactions between the constituent elements of the generator. Specifically, elements placed too closely together would when submerged in a conductive solution lead to a mutual neutralization of the battery effect. It is therefore necessary to space the elements containing the copper/zinc pairs apart by a sufficient and therefore resistive distance. In addition, this spacing is useful in order to obtain a progression as a function of the impregnation of the protection. The fundamental role of the last unit as a conductor triggering the turn-on of the luminous change indicator on total dorsal saturation will once again be noted. Using, instead of a textile, a flexible printed circuit board with etched copper electrodes and insulated interconnecting tracks coupled to the adhesively bonded zinc electrodes, forming the units, provides straight away the resistive spacing between pairs without the electrodes being able to move as they are etched and held on the printed circuit board.

BRIEF DESCRIPTION OF THE DRAWINGS

The present invention will be described in greater detail with reference to the accompanying drawings in which.

DESCRIPTION OF THE PREFERRED EMBODIMENTS

Figure 1:
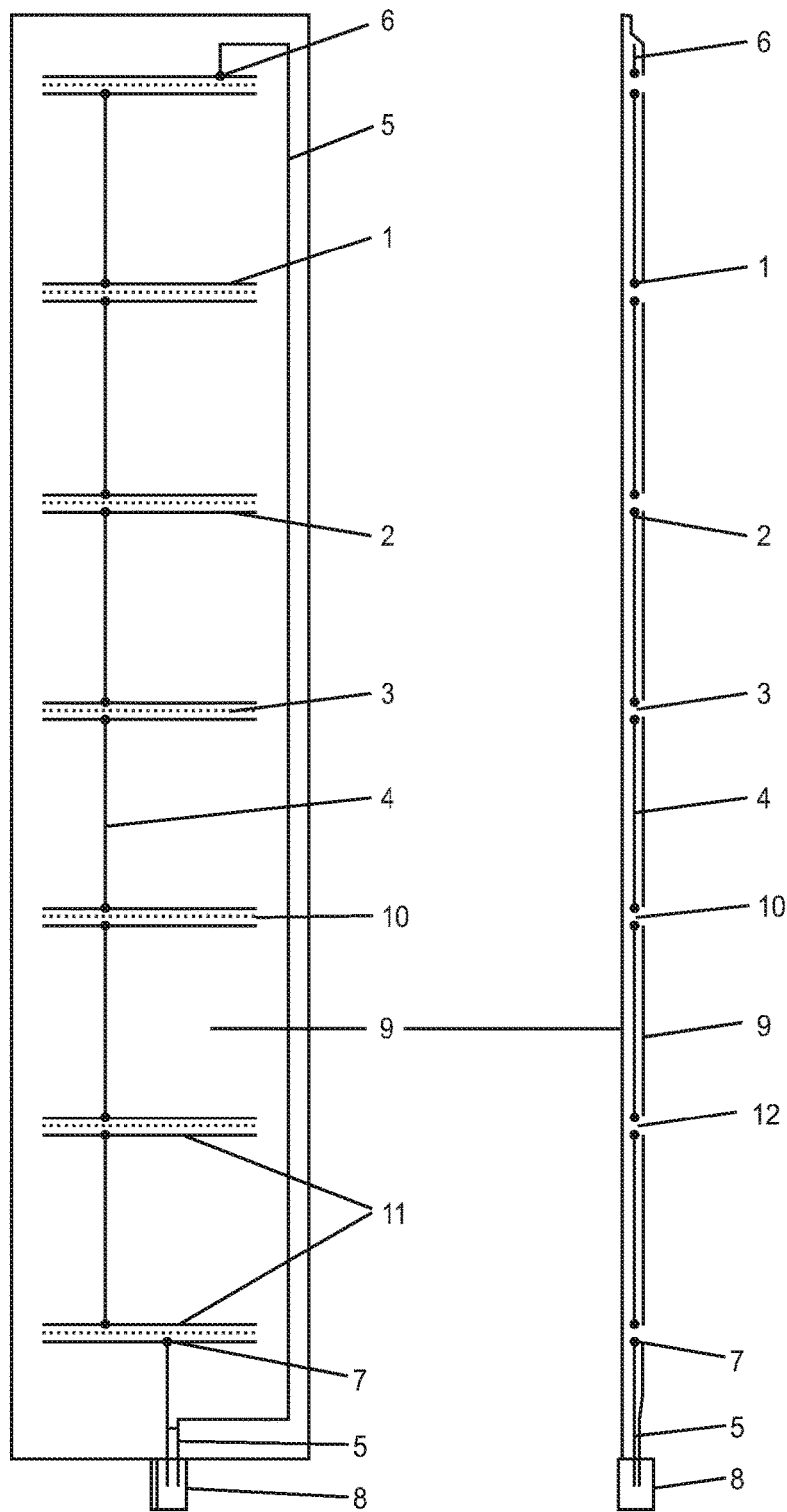
FIG. 1 is a cross-sectional view front above of the generator module forming the present invention.

The following drawings illustrate the invention:

FIG. 1 shows in cross section and as viewed from above a generator module with its elements. The elements are composed of a flat copper wire (1) separated from a flat zinc wire (2) by a very thin space (3). A sheathed conductive wire (4) is soldered in order to interconnect the elements together electrically. At the ends of the generator, sheathed conductive wires (5) are soldered to the final electrodes (copper (6) on the one hand and zinc (7) on the other) to be connected to the external connector of the protection (8). The elements are fastened to a semipermeable flexible textile (9). Perforated orifices allow the inter-electrode space (10) to be imbibed. The distance (11) separating the paired elements makes it possible to prevent any interactions therebetween that would cancel out the battery effect. It is possible to add a weak acid powder (12) to the inter-electrode spaces in order to ensure a low pH by dissolution in a too neutral or weakly basic urine.

Figure 2:
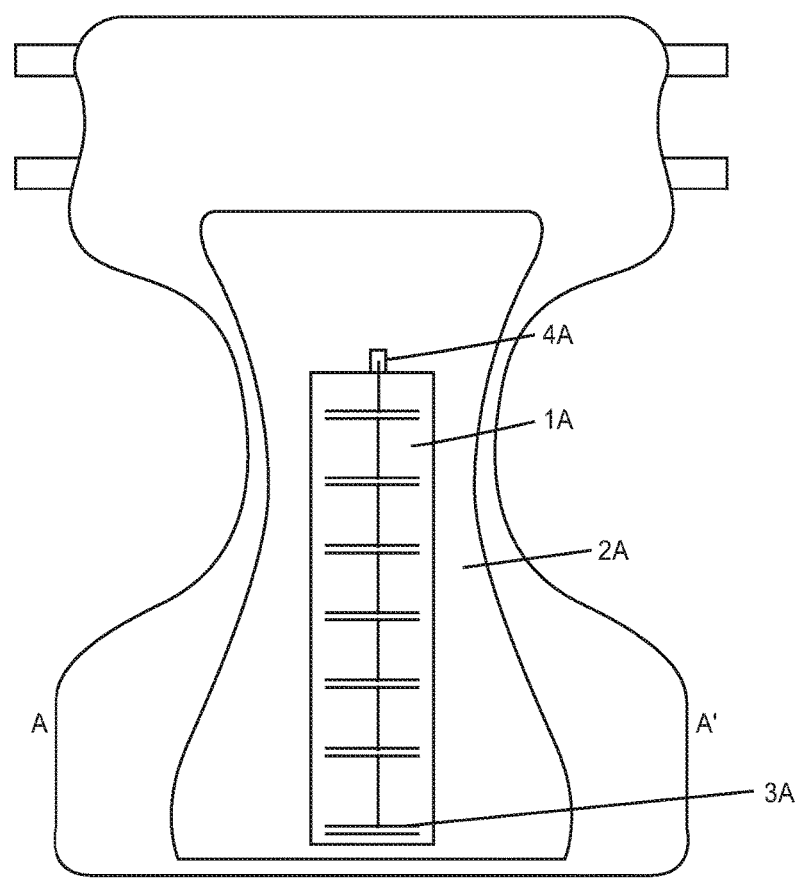
FIG. 2 is a cross-sectional view from above of protection containing the generator module.
Figure 2:

FIG. 2 shows in cross section and from above a protection containing a current generator module. The generator (1A) is integrated into the absorbent liner of the protection (2A). The last element of the generator (3A) is placed at the dorsal boundary of the absorbent portion. A biased electrical connector (4A) protrudes from the protection on the front side thereof facing the hypogastric anatomical region.

Figure 3:
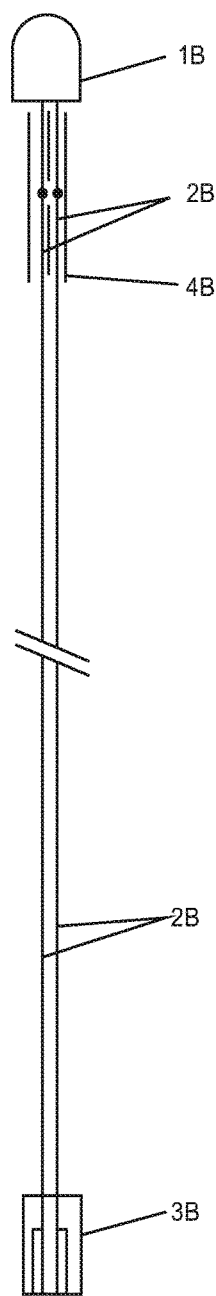
FIG. 3 illustrates a wired indicator.

FIG. 3 shows a wired indicator. A light-emitting diode (1B) is soldered to one of the ends of a bipolar conductive wire (2B). A connector (3B) is soldered to the other end of the conductive wire. The solder joints are insulated by a thermoplastic collar (4B).

Figure 4:
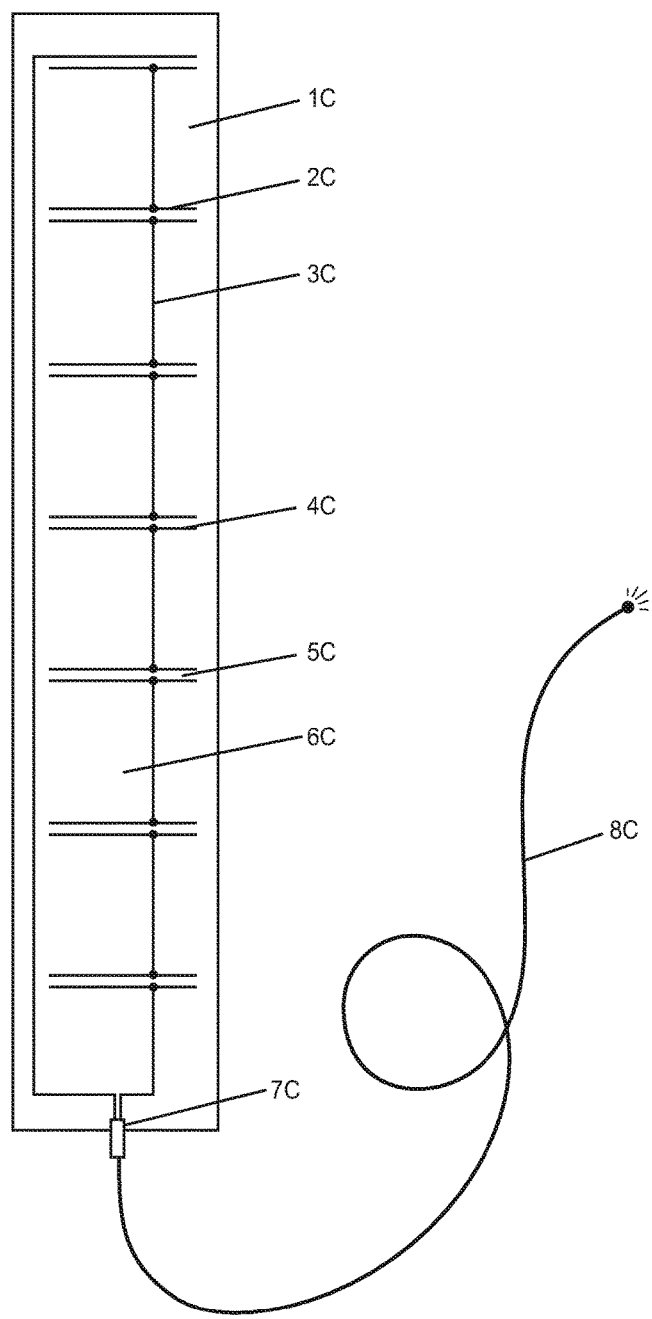
FIG. 4 illustrates a printed circuit board.

FIG. 4 illustrates the printed circuit board version. A very thin epoxy printed circuit board (1C) is etched with uninsulated electrode tracks (2C). The same side possesses interconnecting tracks insulated by a lacquer (3C) and connecting the electrodes in series; adhesively bonded zinc electrodes (4C) made up of a thin wire or by a conductive zinc-based coating (galvanization) are placed next to the copper electrodes. A minimal space is left between the electrodes (5C) so that the acid urine bathes the metals in order to induce the expected redox reaction. Likewise, the distance between the electrochemical units (6C) may be adjusted as desired to obtain the resistance required to isolate the pairs—this proves to be easier with epoxy as it is an excellent insulator. At the end in this version a light-emitting LED indicator (7C) is soldered to the printed circuit board, an optical fiber (8C) that will convey the photons a distance away from the patient possibly being connected. Any other indicator device may be envisioned, as mentioned above.

By way of nonlimiting example, the dimensions of the generator module on a flexible textile will be: 30 centimeters long by 5 centimeters wide and 0.01 centimeters thick. The electrodes are produced from flat wires of 0.50 millimeters side and 4.5 centimeters length. The inter-electrodes space will be as small as possible without contact. The distance between the elements of the battery will be 4 centimeters minimum in order to prevent interference and obtain a gradation in the voltage increase depending on the saturation.

The invention claimed is:

1. An autonomous electronic device for detecting and signaling the saturation of a protective liner type article intended for urofecal incontinence, comprising at least one autonomous electrical generator module comprising an arrangement of pairs of metal electrode elements that are electrically connected to one another and distributed over a preset internal zone of the article, each pair of metal electrode elements being able to generate a current on contact with an aqueous and acid urofecal medium via a redox reaction, and wherein the generated current gradually increases and is released to electrically and autonomously control internal or external means for signaling the saturation, only when a last pair of metal electrode elements in the arrangement of inks is wetted, and wherein the means for signaling the saturation are luminous and/or sonic.

2. The device as claimed in claim 1, wherein the pairs of metal electrode elements are connected in series electrically with a minimum distance between each pair preventing interactions, the output connection terminals being the first electrode of the first pair and the second electrode of the last pair.

3. The device as claimed in claim 1, wherein each electrode element made up of parallel strips of a pair being separated one from the other by a parallel space receiving the urofecal medium, ensuring the autonomy of the pairs by preventing any electrical interference between them.

4. The device as claimed in claim 1, wherein the last pair of electrodes of the arrangement is located in the dorsal boundary portion of the protective liner type article to provide the generator assembly with an on/off switch function that is activated when the on/off switch is wetted to indicate the saturation of the protective liner type article.

5. The device as claimed in claim 1, wherein the generator assembly is completely or partially integrated into a textile envelope comprising pores in zones facing the spaces separating the electrodes.

6. The device as claimed in claim 1, wherein the electrical generator module comprises a thin flexible printed circuit board type structure comprising one or more sides of conductive tracks of one or more materials.

7. The device as claimed in claim 1, wherein the signaling means comprise at least one internal or external light-emitting diode powered only by the generator module.

8. The device as claimed in claim 1, wherein the signaling means comprise at least one internal light source of the light-emitting diode type associated optically with an optical-fiber-comprising means for transmitting the information over distance.

9. The device as claimed in claim 1, wherein the electrical generator module extends along the longitudinal central axis of the protective liner type article intended for incontinence with at least one major portion located toward the back portion of the article.

10. The device as claimed in claim 1, wherein the electrical generator module has a strip format consisting of an arrangement of electrode pairs perpendicular and symmetric relative to the central axis, the pairs being spaced apart by a preset distance.

11. The device as claimed in claim 2, wherein each electrode element made up of parallel strips of a pair being separated one from the other by a parallel space receiving the urofecal medium, ensuring the autonomy of the pairs by preventing any electrical interference between them.

12. The device as claimed in claim 11, wherein the last pair of electrodes of the arrangement is located in the dorsal boundary portion of the protective liner type article to provide the generator assembly with an on/off switch function that is activated when the on/off switch is wetted to indicate the saturation of the protective liner type article.

13. The device as claimed in claim 3, wherein the last pair of electrodes of the arrangement is located in the dorsal boundary portion of the protective liner type article to provide the generator assembly with an on/off switch function that is activated when the on/off switch is wetted to indicate the saturation of the protective liner type article.

14. The device as claimed in claim 2, wherein the last pair of electrodes of the arrangement is located in the dorsal boundary portion of the protective liner type article to provide the generator assembly with an on/off switch function that is activated when the on/off switch is wetted to indicate the saturation of the protective liner type article.

15. The device as claimed in claim 14, wherein the generator assembly is completely or partially integrated into a textile envelope comprising pores in zones facing the spaces separating the electrodes.

16. The device as claimed in claim 13, wherein the generator assembly is completely or partially integrated into a textile envelope comprising pores in zones facing the spaces separating the electrodes.

17. The device as claimed in claim 12, wherein the generator assembly is completely or partially integrated into a textile envelope comprising pores in zones facing the spaces separating the electrodes.

18. The device as claimed in claim 11, wherein the generator assembly is completely or partially integrated into a textile envelope comprising pores in zones facing the spaces separating the electrodes.

19. The device as claimed in claim 4, wherein the generator assembly is completely or partially integrated into a textile envelope comprising pores in zones facing the spaces separating the electrodes.

20. The device as claimed in claim 3, wherein the generator assembly is completely or partially integrated into a textile envelope comprising pores in zones facing the spaces separating the electrodes.

21. An autonomous electronic device for detecting and signaling the saturation of a protective liner type article intended for urofecal incontinence, comprising at least one autonomous electrical generator module comprising an arrangement of pairs of metal electrode elements that are electrically connected to one another in series with a minimum distance between each pair preventing interaction, and distributed over a preset internal zone of the article, the output connection terminals of the generator module being the first electrode of the first pair and the second electrode of the last pair each pair of metal electrode elements being able to generate a current on contact with an aqueous and acid urofecal medium via a redox reaction, to electrically and autonomously control internal or external means for signaling the saturation, these means being luminous and/or sonic.

22. An autonomous electronic device for detecting and signaling the saturation of a protective liner type article intended for urofecal incontinence, comprising at least one autonomous electrical generator module comprising an arrangement of pairs of metal electrode elements that are electrically connected to one another and distributed over a preset internal zone of the article, each pair of metal electrode elements being able to generate a current on contact with an aqueous and acid urofecal medium via a redox reaction, to electrically and autonomously control internal or external means for signaling the saturation, these means being luminous and/or sonic, and wherein the luminous signaling means comprise at least one internal light source of the light-emitting diode type associated optically with an optical-fiber-comprising means for transmitting the information over distance.

* * * * *